United States Patent [19]

Fisher et al.

[11] Patent Number: 5,468,867

[45] Date of Patent: Nov. 21, 1995

[54] PROCESS FOR PREPARING1-BUTYL-2-[2'-(2H-TETRAZOL-5-YL)BIPHENYL-4-YLMETHYL1-1H-INDOLE-3-CARBOXYLIC ACID

[75] Inventors: Lawrence E. Fisher, Mountain View; Lee A. Flippin, Woodside; Michael G. Martin, San Francisco, all of Calif.

[73] Assignee: Syntex (U.S.A.) Inc., Palo Alto, Calif.

[21] Appl. No.: 250,129

[22] Filed: May 27, 1994

[51] Int. Cl.⁶ ................................................. C07D 471/04

[52] U.S. Cl. ........................ 548/253; 548/250; 548/252

[58] Field of Search ................................ 548/253, 252, 548/250

[56] References Cited

U.S. PATENT DOCUMENTS 5,093,346 3/1992 Carini et al. .................. 514/381
5,124,335 6/1992 Patchett et al. .................. 514/300

FOREIGN PATENT DOCUMENTS

0516392A2 12/1992 European Pat. Off. .

OTHER PUBLICATIONS

Carini, D. J., et al., "Nonpeptide Angiotensin II Receptor Antagonists: The Discovery of a Series of N–(Biphenylylmethyl) imidazoles as Potent, Orally Active Antihypertensives", *J. Med. Chem.* (1991), vol. 34, No. 8, pp. 2525–2547.

*Primary Examiner*—David B. Springer
*Attorney, Agent, or Firm*—Wayne W. Montgomery

[57] ABSTRACT

The present invention relates to a process for preparing 1-butyl-2-[2'-(2H-tetrazol-5-yl)biphenyl-4-ylmethyl]-1H-indole-3-carboxylic acid and to intermediates useful in such process.

17 Claims, No Drawings

PROCESS FOR PREPARING1-BUTYL-2-[2'-(2H-TETRAZOL-5-YL)BIPHENYL-4-YLMETHYL1-1H-INDOLE-3-CARBOXYLIC ACID

BACKGROUND OF THE INVENTION

1. Field of the Invention

This invention relates to a novel process for preparing 1-butyl-2-[2'-(2H-tetrazol-5 -yl)biphenyl-4-ylmethyl]-1H-indole-3-carboxylic acid, an angiotensin II receptor antagonist. This invention also relates to novel intermediates useful in the synthesis of 1-butyl-2-[2'-(2H-tetrazol-5-yl)-biphenyl-4-ylmethyl] -1H-indole-3-carboxylic acid and the processes for the preparation of such intermediates.

2. Description of the Field

The renin-angiotensin system is a fundamental physiological mechanism for regulating blood pressure in mammals. Angiotensinogen is secreted into the bloodstream by the liver. Angiotensinogen is then cleaved by the protease renin to yield the decapeptide angiotensin I, which in turn is hydrolyzed by angiotensin converting enzyme (ACE) to the octapeptide angiotensin II.

Angiotensin I is inactive in the cardiovascular system, but angiotensin II has numerous effects. For example, angiotensin II stimulates the adrenal cortex to secrete aldosterone, which causes the kidneys to retain sodium and water, increasing blood pressure. Angiotensin II also causes arteriolar vasoconstriction and facilitates neurotransmission in the sympathetic nervous system. In addition to its effects on the cardiovascular system, angiotensin II contracts gastrointestinal smooth muscle, produces glycogenolysis, alters renal function and produces various CNS effects. The effects of angiotensin II are mediated by the activation of specific angiotensin II receptors located in smooth muscle, adrenal medulla, brain, liver and kidney tissues. The angiotensin II receptor is presently delineated into two major subtypes (i.e., AT-1 and AT-2 receptor subtypes). Angiotensin II receptor antagonists, particularly those which selectively block AT-1 or AT-2 receptor subtypes, are useful in treating diseases which may be ameliorated by a decrease in the physiological effects of angiotensin II.

Various angiotensin II receptor antagonists are known. See, for example, U.S. Pat. Nos. 4,333,943, 4,880,804, 5,053,329, 5,124,335, and European Patents 0 245 637, 0 253 310, and 0 291 969, and also Wong et al. *Hypertension* 1990, 15, 459, *J. Pharmacol. Exp. Ther.* 1990, 256, 211, and Chiu et al., *Biochem. Biophys. Res. Comm.* 1989, 165, 196–203. Substituted indole compounds and derivatives thereof (e.g., 1-butyl-2-[2'-(2H-tetrazol-5-yl)biphenyl-4-ylmethyl] -1H-indole-3-carboxylic acid) are angiotensin II receptor antagonists and are disclosed as such in U.S. Pat. No. 5,212,195 and pending U.S. patent application Ser. No. 08/004,869.

The disclosures of these and other documents referred to throughout this application (e.g., in the Pharmacology section of the Detailed Description of the Invention) are incorporated in this application by reference.

SUMMARY OF THE INVENTION

The present invention relates to a process for the preparation of 1-butyl-2-[2'-(2 H-tetrazol-5-yl)biphenyl-4-ylmethyl]-1H-indole-3-carboxylic acid which process comprises:

(A) (i) treating 1-butyl-1H-indole-3-carboxylic acid with an organometallic base to give 2-metalated 1-butyl-1H-indole-3-carboxylic acid, (ii) optionally treating the 2-metalated 1-butyl-1H-indole-3-carboxylic acid with a metal halide to give 2-transmetalated 1-butyl-1H-indole-3-carboxylic acid, and (iii) reacting the 2-metalated or 2-transmetalated 1-butyl-1H-indole-3-carboxylic acid with protected 2'-(2H-tetrazol-5-yl)biphenyl-4-carbaldehyde to give protected 1-butyl-2-[2'-(2H-tetrazol-5-yl)biphenyl-4-yl(hydroxy)methyl]-1H-indole-3 -carboxylic acid;

(B) dehydroxylating to give protected 1-butyl-2-[2'-(2H-tetrazol-5-yl)-biphenyl-4 -ylmethyl]-1H-indole-3-carboxylic acid and (C) deprotecting.

A second aspect of this invention relates to a process for the preparation of protected 2'-(2H-tetrazol-5-yl)biphenyl-4-carbaldehyde, which process comprises:

(i) treating a compound of Formula I:

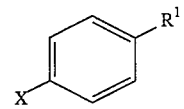

in which X is halo and $R^1$ is 1-isopropyl-2-methylpropyliminomethyl or dimethoxymethyl with an organometallic base to give a corresponding para-metalated intermediate, (ii) optionally treating the para-metalated intermediate with a metal halide to give a para-transmetalated intermediate;

(iii) reacting the para-metalated or para-transmetalated intermediate with a compound of Formula II:

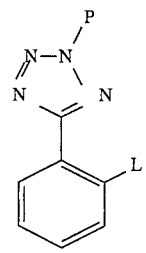

in which L is a leaving group and P is a protective group, and acidifying.

A third aspect of this invention relates to a compound which is protected 2'-(2H-tetrazol-5-yl)biphenyl-4-carbaldehyde and its use in the preparation of 1-butyl-2-[2'-(2H-tetrazol-5-yl)biphenyl-4-ylmethyl]-1H-indole-3-carboxylic acid.

A fourth aspect of this invention is a compound of Formula II and its use in the preparation of protected 2'-(2H-tetrazol-5-yl)biphenyl-4-carbaldehyde.

DETAILED DESCRIPTION OF THE INVENTION

Definitions:

As used in this application:

"Halo" means bromo, chloro, fluoro or iodo.

"Leaving group" has the meaning conventionally associated with it in synthetic organic chemistry, i.e., an atom or group displaceable under alkylating conditions, and includes halo, $(C_{1-4})$alkyloxy (e.g., methoxy, ethoxy and the like), aryloxy (e.g., phenoxy and the like), $(C_{1-4})$alkylthio (e.g., methylthio, ethylthio and the like), arylthio (e.g., phenylthio and the like) and alkane- or arenesulfonyloxy (e.g., mesyloxy, ethanesulfonyloxy, benzenesulfonyloxy, trifluoromethanesufonyloxy, tosyloxy and the like).

"Organometallic base" means a base capable of reacting with an organic compound to give a "metalated" compound of the formula R-Met$^1$ in which Met$^1$ is any monovalent electro positive metal element, typically an alkylmetalic base and preferably an alkyl alkali metal base (e.g., n-butyllithium, n-butylsodium, n-butylpotassium, lithium diisopropylamide (LDA) and the like). A "lithiated" compound means a metalated compound of the formula R-Met$^1$ in which Met$^1$ is —Li.

"Metal halide" means a halide of any multivalent electro positive metal element capable of reacting with a metalated organic compound to give a "transmetalated" compound of the formula R-Met$^2$(X)$_{n-1}$ in which Met$^2$ is the multivalent metal element, X is halo, and n corresponds to the valence of the metal (e.g., —MgCl, —ZnCl, NiCl, —ZnBr, —AlCl$_2$, etc.) and includes magnesium chloride, magnesium iodide, magnesium bromide, zinc chloride, zinc iodide, zinc bromide, copper chloride, copper iodide, copper bromide, nickel chloride, nickel iodide, nickel bromide, aluminum chloride, aluminum iodide, aluminum bromide and the like.

"Transmetalation" means the process of reacting a metal halide with a metalated compound to give a transmetalated compound.

"Optional" or "optionally" means that the subsequently described event or circumstance may or may not occur, and that the description includes instances where the event or circumstance occurs and instances in which it does not. For example, "optionally treating the para-metalated intermediate" means that the treatment with metal halide may or may not be carried out in order for the process described to fall within the invention, and the invention includes those processes wherein the treatment occurs and those processes in which it does not.

"Protective group" has the meaning conventionally associated with it in synthetic organic chemistry, i.e., a group which selectively blocks one reactive site in a multifunctional compound such that a chemical reaction can be carried out selectively at another unprotected reactive site and which can be readily removed after the selective reaction is completed. Certain intermediates used in the processes described in this application contain a tetrazol-5-yl moiety in which a reactive nitrogen atom is present. The reactive site in the tetrazol-5-yl moiety can be protected with an acceptable protective group (e.g., 1,1-dimethylethyl, 1-methyl-1-phenylethyl, triphenylmethyl, etc.) which can then be removed by catalytic reduction or chemical cleavage after the selective reaction is completed. The 1-methyl-1-phenylethyl protective group is particularly resistant to cleavage during the selective reaction and is preferred.

"Protective agent" means an agent which will react with a multifunctional compound and create a protective group at reactive nitrogen atoms.

"Protected" in reference to a compound or a group means a derivative of compound or group in which reactive nitrogens are blocked with protective groups.

"Deprotecting" refers to removing any protective groups present after the selective reaction has been carried out.

Certain compounds described in this application contain a tetrazolyl group. The tetrazolyl moiety exists in tautomeric equilibrium between the 1H-tetrazol-5-yl and the 2H-tetrazol-5-yl tautomers. The protected tetrazole group exists as a mixture of the protected 1H-tetrazol-5-yl and 2H-tetrazol-5-yl isomers. Upon removal of the protective group the tetrazolyl group reverts to a tautomeric equilibrium. The compounds which contain the tetrazolyl group or its protected derivative are named, illustrated or otherwise described in this application as the 2H-tetrazolyl tautomer or the protected 2H-tetrazolyl isomer, respectively. However, it is to be understood that the 1H-tetrazolyl tautomers and isomers are encompassed by such names, illustrations and descriptions as well.

The compound of the Formula VII:

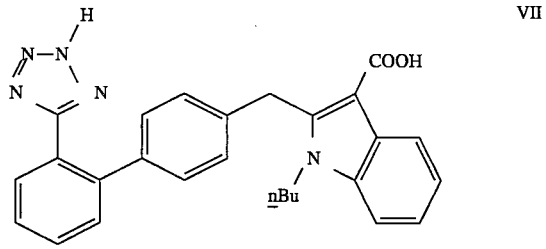

is named 1-butyl-2-[2'-(2H-tetrazol-5-yl)biphenyl-4-ylmethyl]-1H-indole-3-carboxylic acid and is described in U.S. Pat. No. 5,212,195 as a angiotensin II receptor antagonist.

Preferred Embodiments:

While the broadest definition of this invention is set forth in the Summary of the Invention, certain compounds of Formula II, the protective groups of the protected 2'-(2H-tetrazol-5-yl)biphenyl-4-carbaldehyde and procedures for carrying out the processes of this invention are preferred. Preferred compounds of Formula II are those in which L is methoxy. A preferred protective group of the protected 2'-(2H-tetrazol-5-yl)biphenyl-4-carbaldehyde is 1-methyl-1-phenylethyl.

A preferred process for the preparation of protected 2'-(2H-tetrazol-5-yl)biphenyl-4-carbaldehyde comprises:

(i) treating (4-bromobenzylidene) (1-isopropyl-2-methylpropyl)amine with n-butyllithium to give para-lithiated (benzylidene) (1-isopropyl-2-methylpropyl)amine and (ii) reacting the para-lithiated (benzylidene) (1-isopropyl-2-methylpropyl)amine with 5-(2-methoxyphenyl)-2-(1-methyl-1-phenylethyl)-2H-tetrazole and acidifying.

A preferred process for the preparation of 1-butyl-2-[2'-(2H-tetrazol-5 -yl)biphenyl-4-ylmethyl]-1H-indole-3-carboxylic acid comprises:

(A) (i) treating 1-butyl-1H-indole-3-carboxylic acid with n-butyllithium to give 2-lithiated 1-butyl-1H-indole-3-carboxylic acid and (ii) reacting the 2-lithiated 1-butyl-1H-indole-3-carboxylic acid with protected 2'-[2-(1-methyl-1-phenylethyl)-2H-tetrazol-5-yl]biphenyl-4-carbaldehyde to give 1-butyl-2-{2'-[2-(1-methyl-1-phenylethyl)-2H-tetrazol-5-yl] biphenyl-4-yl(hydroxy)methyl}-1H-indole-3-carboxylic acid;

(B) dehydroxylating to give 1-butyl-2-{2'-[2-(1-methyl-1-phenylethyl)-2H-tetrazol-5 -yl]biphenyl-4-ylmethyl}-1H-indole-3-carboxylic acid and (C) deprotecting;

preferably wherein deprotecting comprises reacting the 1-butyl-2-{2'-[2 -(1-methyl-1-phenylethyl)-2H-tetrazol-5-yl]biphenyl-4-ylmethyl}-1H-indole-3-carboxylic acid with a Lewis acid in the presence of a thiol, preferably wherein the Lewis acid is boron trifluoride etherate, tin(IV)chloride, titanium(IV)chloride, titanium(III)chloride, zinc chloride or selenium(IV)chloride, preferably boron trifluoride etherate, and the thiol is methyl thioglcolate, (C$_{1-4}$)alkanethiol, arylthiol, 2-mercaptoacetic acid, (C$_{1-4}$)alkyl 2-mercaptoacetate or pentaerythritol tetra (2-mercaptoacetate), preferably methyl thiogylcolate or pentaerythritol tetra(2-mercaptoacetate). Processes for preparing 1-butyl-2-[2'-(2H-tetrazol-5-yl)biphenyl-4-ylmethyl]-1H-indole-3 -carboxylic acid:

While the present invention has been described with respect to specific embodiments thereof, it will be understood by those skilled in the art that various changes may be made and equivalents may be substituted without departing from the true spirit and scope of the invention. All such modifications are intended to be within the scope of the claims appended to this application.

The process of the invention is depicted by the following reaction scheme:

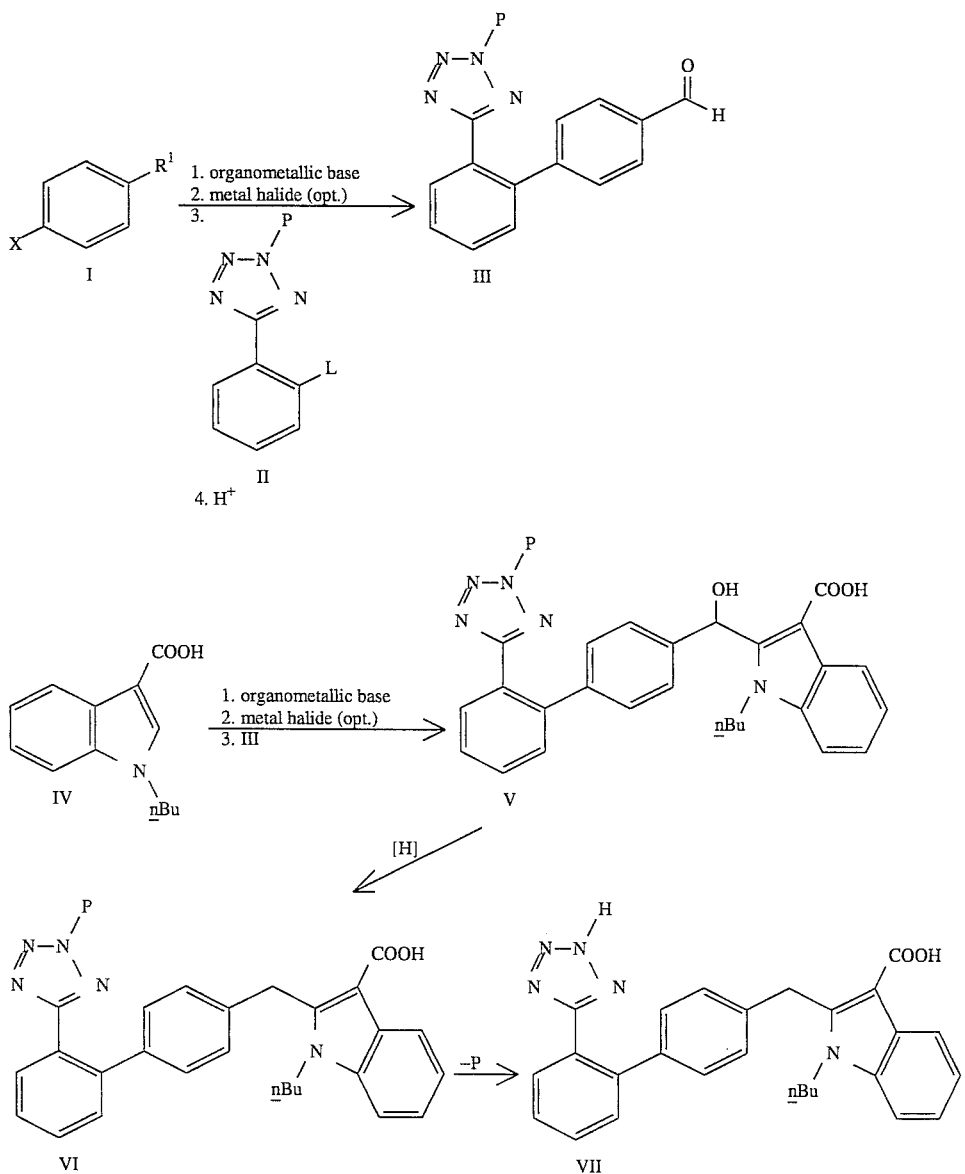

in which L, P, X and $R^1$ are as defined in the Summary of the Invention.

1-Butyl-2-[2'-(2H-tetrazol-5-yl)biphenyl-4-ylmethyl]-1H-indole-3-carboxylic acid (Formula VII) can be prepared by reacting 2-metalated or 2-transmetalated 1-butyl-1H-indole-3-carboxylic acid with protected 2'-(2H-tetrazol-5-yl)-biphenyl-4-carbaldehyde (Formula III) to give protected 1-butyl-2-[2'-(2H-tetrazol-5-yl)biphenyl-4-yl(hydroxy)methyl]-1H-indole-3-carboxylic acid (Formula V), dehydroxylating to give protected 1-butyl-2-[2'-(2 H-tetrazol-5-yl)-biphenyl-4-ylmethyl]-1H-indole-3-carboxylic acid (Formula VI) and deprotecting. The 2-metalated 1-butyl-1H-indole-3-carboxylic acid is prepared by cooling a solution of the 1-butyl-1H-indole-3-carboxylic acid (Formula IV) in a suitable solvent, preferably an ether (e.g., tetrahydrofuran (THF), diethyl ether, monoglyme, diglyme, preferably THF), to between −70° and 10° C., typically to between −70° to −50° C. and preferably to approximately −60° C., adding an organometallic base, typically an alkylmetallic base and preferably an alkyl alkali metal base (e.g., n-butyllithium, n-butylsodium, n-butylpotassium, lithium diisopropylamide (LDA), etc., preferably n-butyllithium), at a rate such that the reaction temperature remains below 15° C., preferably below −20° C., and then allowing the reaction to proceed at −70° to 15° C., typically at −20° to 0° C. and preferably at approximately −8° C., for 10 minutes to 5 hours.

The transmetalation and/or the reaction with the protected 2'-(2H-tetrazol-5-yl)biphenyl-4-carbaldehyde is carried out by cooling the solution containing the 2-metalated 1-butyl-1H-indole-3-carboxylic acid to between −70° and 15° C., typically to between −70° to −50° C. and preferably to approximately −60° C., adding a suitable metal halide (e.g., magnesium chloride, zinc chloride, zirconium chloride, etc, preferably zinc chloride) and/or the protected 2'-(2H-tetrazol-5-yl)biphenyl-4-carbaldehyde and then allowing the reaction to proceed at −78° to 0° C., typically at −40° to −20° C. and preferably at approximately −30° C., for 0.15 to 3 hours, preferably approximately 1 hour.

The dehydroxylation can be effected by catalytic hydrogenation (e.g., $H_2$, palladium on carbon; $H_2$, palladium hydroxide, etc.). Preferably the dehydroxylation is carried out with 10% palladium on carbon at 20° C. to 80° C., typically at 40° to 60° C. and preferably at approximately 50° C., and 1 to 300 psi, typically at 150 to 250 psi and preferably at approximately 200 psi, and requires 24 to 72 hours.

Deprotection is effected by any means which removes the protective group from the 2H-tetrazol-5-yl group to give the desired unprotected product in reasonable yield. A detailed description of the techniques applicable to protective groups and their removal can be found in T. W. Greene, *Protective Groups in Organic Synthesis*, John Wiley & Sons, Inc. 1981. For example, a convenient deprotecting method, particularly when the protective group is triphenylmethyl, comprises catalytic hydrogenation under conditions similar to those for the dehydroxylation step described above. The preparation of 1-butyl-2-[2'-(2 H-tetrazol-5-yl)biphenyl-4-ylmethyl]-1H-indole-3-carboxylic acid is described in Example 8.

Another convenient deprotecting method, particularly wherein the protective group is 1-methyl-1-phenylethyl, comprises reacting the protected derivative with 1 to 10 molar equivalents, typically with 2 to 6 molar equivalents and preferably with approximately 4 molar equivalents, of a Lewis acid (e.g., boron trifluoride etherate, tin(IV)chloride, titanium(IV)chloride, titanium(III)chloride, zinc chloride or selenium(IV)chloride, etc., preferably boron trifluoride etherate) in the presence of 1 to 5 molar equivalents, typically 2 to 4 molar equivalents and preferably approximately 3 molar equivalents, of a thiol (e.g., ($C_{1-4}$)alkanethiols such as methanethiol, ethanethiol, 1-propanethiol, 2-propanethiol and the like, arylthiols such as thiophenol and the like, 2-mercaptoacetic acid, ($C_{1-4}$)alkyl 2-mercaptoacetates such as methyl thioglycolate, methyl 2-mercaptoacetate, ethyl 2-mercaptoacetate and the like, pentaerythritol tetrakis(2-mercaptoacetate), etc., preferably methyl thioglycolate or pentaerythritol tetrakis(2-mercaptoacetate)) in a suitable solvent, preferably a nitrile or ether (e.g., acetonitrile, THF, diethylether, etc., preferably acetonitrile). The reaction is carried out at −10° to 50° C., typically at 10° to 40° C. and preferably at approximately 25 ° C., for 0.5 to 15 hours. This deprotecting process is particularly useful for deprotecting protected 1-butyl-2-[2'-(2H-tetrazol-5-yl)biphenyl-4-ylmethyl]-1 H-indole-3-carboxylic acid. The deprotection of 1-butyl-2-{2'-[2-(1-methyl-1-phenylethyl)-2 H-tetrazol-5-yl]biphenyl-4-ylmethyl}-1H-indole-3-carboxylic acid is described in Example 9.

1-Butyl-1H-indole-3-carboxylic acid can be prepared by treating 1H-indole-3-carboxylic acid with an alkali metal hydride (e.g., lithium hydride, potassium hydride, sodium hydride, etc.) in a suitable solvent (e.g., acetamide, dimethylsulfoxide (DMSO), dimethylformamide (DMF), preferably DMF) and then reacting with n-butyl halide, preferably n-butyl bromide. The procedure is carried out by cooling a solution of the alkali metal hydride (1 to 1.5 molar equivalents) to between −20° and 10° C., typically to between −10° and 5° C. and preferably to approximately 0° C., and then slowly adding the 1H-indole-3-carboxylic acid. The reaction mixture is then stirred for 10 minutes to 4 hours, cooled to between −2° and 10° C., typically to −2° to 5° C. and preferably to approximately 0° C., and then the n-butyl halide (1 to 1.5 molar equivalents) is added. The preparation of 1-butyl-1H-indole-3-carboxylic acid is described in Example 7.

The protected 2'-(2H-tetrazol-5-yl)biphenyl-4-carbaldehyde is prepared by reacting an appropriate para-metalated or para-transmetalated intermediate with a compound of Formula II and then acidifying. The para-metalated intermediate is prepared by cooling a solution of Formula I in a suitable solvent, preferably an ether (e.g., THF, diethyl ether, dioxane, preferably THF), to between −75° to 25° C., typically to between −70° to −50° C. and preferably to approximately −60° C., and then adding to the solution an organometallic base, typically an alkylmetallic base and preferably an alkyl alkali metal base (e.g., n-butyllithium, n-butylsodium, n-butylpotassium, lithium diisopropylamide (LDA), etc., preferably n-butyllithium) at a rate such that the reaction temperature remains below 0° C., preferably below −40° C., and then allowing the reaction to proceed at −40° to 25° C., typically at −10° to 10° C. and preferably at approximately 0° C., for 15 minutes to 2 hours.

The transmetalation and/or the reaction with the compound of Formula II is carried out by cooling the solution containing the para-metalated intermediate to between −78° and 0° C., typically to between −45° to 0° C. and preferably to approximately 0° C., and then adding a suitable metal halide (e.g., magnesium chloride, zinc chloride, zirconium chloride, etc, preferably zinc chloride) and/or compound of Formula II and then allowing the reaction to proceed at 0° to 30° C., typically at 15° to 30° C. and preferably at approximately 22° C., for 15 minutes to 2 hours. The acidification can be carried out with dilute hydrochloric acid in a suitable solvent (e.g., 1:1 water/THF, methanol, etc.) at 25° to 50° C. and requires 15 minutes to 4 hours. The preparation of protected 2'-(2H-tetrazol-5-yl)biphenyl-4-carbaldehyde is described in Examples 5 and 6.

Compounds of Formula I in which $R^1$ is 1-isopropyl-2-methylpropyliminomethyl can be prepared by reacting an appropriate halogenated benzaldehyde with 2,4-dimethylpent-3-ylamine in a suitable solvent, preferably toluene, at reflux for 1 to 14 hours. Compounds of Formula I in which $R^1$ is dimethoxymethyl can be prepared by reacting an appropriate halogenated benzaldehyde with trimethyl orthoformate in a suitable solvent, preferably methanol, at reflux for 1 to 14 hours. The preparation of a compound of Formula I in which $R^1$ is either 1-isopropyl-2-methylpropyliminomethyl or dimethoxymethyl is described in Examples 1 and 2, respectively.

The compounds of Formula II can be prepared from the appropriate 2-substituted 1-cyanobenzene. For example a compound of Formula II in which L is methoxy can be prepared by reacting 1-cyano-2-methoxybenzene with tributyltin azide to give 5-(2-methoxyphenyl)-2H-tetrazole and then creating an appropriate protective group. The reaction with the azide is carried out in a suitable solvent, preferably xylene, at reflux and requires 4 to 24 hours. The protective group can be created by reacting the tetrazole with 1 to 2 molar equivalents of a suitable protective agent (e.g. 2-methyl-2-propanol, 2-phenyl-2-propanol, α-methylstyrene, trephenymethylchloride etc.) in a suitable solvent (e.g., trifluoroacetic acid, trichloroacetic acid in methylene chloride, etc.) at 0° to 30° C., typically 15° to 30° C. and preferably at approximately 25° C., for 1 to 14 hours. The preparation of a compound of Formula II is described in Examples 3 and 4.

EXAMPLE 1

(4-Bromobenzylidene)(1-isopropyl-2-methylpropyl)amine

The following is the preparation of a compound of Formula I in which X is bromo and $R^1$ is 1-isopropyl-2-methylpropyliminomethyl.

A mixture of 4-bromobenzaldehyde (7.3 g, 40.0 mmol), 2,4-dimethylpent-3-ylamine (4.8 g, 41.4 mmol), and para-toluenesulfonic acid (0.05 g, 0.29 mmol) in 125 mL of toluene was heated under reflux while water was removed with a Dean-Stark trap. The toluene then was removed under vacuum and distillation of the remaining residue gave (4-bromobenzylidene)(1-isopropyl-2-methylpropyl)amine (10.71 g) as a clear colorless oil.

EXAMPLE 2

1-Bromo-4-(dimethoxymethyl)benzene

The following is the preparation of a compound of Formula I in which X is bromo and $R^1$ is dimethoxymethyl.

A mixture of 4-bromobenzaldehyde (21.9 g, 120 mmol), methyl orthoformate (50 mL, 457 mmol), and para-toluenesulfonic acid (0.05 g, 0.29 mmol) in 100 mL of methanol was heated under reflux for 5 hours. The solvent was removed under vacuum and distillation of the remaining residue gave 1-bromo-4-(dimethoxymethyl)benzene (2.24 g, 9.7 mmol) as a clear colorless oil.

EXAMPLE 3

1-(1,1-Dimethylethyl)-5-(2-methoxyphenyl)-2H-tetrazole

The following is the preparation of a compound of Formula II in which L is methoxy and P is 1,1-dimethylethyl.
Step (a)

A mixture of 1-cyano-2-methoxybenzene (1.02 g, 7.7 mmol) and tributyltin azide (3.4 g, 10.0 mmol) in 3.0 mL of xylene was heated under reflux for 5 hours. The reaction mixture then was cooled and diluted with diethyl ether. Anhydrous hydrochloric acid was bubbled into the mixture and a white precipitate formed. The precipitate was collected by suction filtration and washed repeatedly with diethyl ether. Drying gave 5-(2-methoxyphenyl)-2H-tetrazole (1.33 g, 7.55 mmol).
Step (b)

A mixture of 5-(2-methoxyphenyl)-2H-tetrazole (0.83 g, 4.71 mmol), 2-methyl-2-propanol (0.7 g, 9.4 mmol), and sulfuric acid (0.24 g, 2.4 mmol) in 4.6 mL of TFA was stirred under nitrogen at room temperature for 16 hours. The reaction mixture then was diluted with ethyl acetate, poured into 2M potassium hydroxide, and extracted with ethyl acetate. The ethyl acetate layer was washed with water, dried over magnesium sulfate and concentrated. Purification of the residue by column chromatography on silica gel (elution: 10% ethyl acetate/hexane) gave 1-(1,1-dimethylethyl)-5-(2-methoxyphenyl)-2H-tetrazole (0.5102 g, 1.67 mmol), as an oil.

Proceeding as in Example 3 but replacing 2-methyl-2-propanol with 2-phenyl-2-propanol gave 5-(2-methoxyphenyl)-1-(1-methyl-1-phenylethyl)-2H-tetrazole as an oil.

EXAMPLE 4

5-(2-Methoxyphenyl)-1-triphenylmethyl-2H-tetrazole

The following is the preparation of a compound of Formula II in which L is methoxy and P is triphenylmethyl.

A mixture of 5-(2-methoxyphenyl)-2H-tetrazole (1.0 g, 5.7 mmol), prepared as in Example 3, Step (a), and sodium hydride (0.8 g) in 20 mL of 1-methyl-2-pyrrolidinone was stirred under hydrogen and triphenylmethyl chloride (1.5 g, 5.4 mmol) was added. The mixture was stirred for 2 hours and then poured into water. The mixture was filtered and the filtered residue was dissolved in methylene chloride. Purification of the residue by column chromatography on silica gel (elution: 20% ethyl acetate) gave 5-(2-methoxyphenyl)-1-triphenylmethyl-2H-tetrazole (1.2 g, 2.9) m.p. 165°–170° C.

EXAMPLE 5

2'-[2-(1,1-Dimethylethyl)-2H-tetrazol-5-yl]biphenyl-4-carbaldehyde

The following is the preparation of a protected 2'-(2H-tetrazol-5-yl)-biphenyl-4-carbaldehyde in which the protective group is 1,1-dimethylethyl.

A solution of (4-bromobenzylidene)(1-isopropyl-2-methylpropyl)amine (1.41 g, 5.0 mmol), prepared as in Example 1, in 5.0 mL of dry diethyl ether was cooled to −55° C. and n-butyllithium (3.2 mL, 1.6M in hexane, 5.0 mmol) was added over 5 minutes. The mixture was allowed to warm to −40° C. and held at that temperature for 15 minutes. The mixture was then allowed to warm to −15° C. over 10 minutes and 1-(1,1-dimethylethyl)-5-(2-methoxyphenyl)-2H-tetrazole (0.683 g, 0.294 mol), prepared as in Example 3, in 2.0 mL of diethyl ether was added rapidly. The mixture was allowed to warm to 22° C., allowed to stand for 45 minutes and 50 mL of saturated ammonium chloride was added. The mixture was diluted with 150 mL of diethyl ether and washed twice with 150 mL of saturated ammonium chloride and once with 100 mL of water. The diethyl ether layer was dried over magnesium sulfate and concentrated. The residue was dissolved in 0.5 mL of 12.0M hydrochloric acid, 20 mL of THF and 20 mL of water and the solution was heated under reflux on a steam bath for 30 minutes. The reaction mixture was cooled and extracted three times with 100 mL of diethyl ether. The combined diethyl ether layers were dried over magnesium sulfate, filtered and concentrated. Purification of the residue by column chromatography on silica gel (elution: 10% ethyl acetate/hexane) gave 2'-[2-(1,1-dimethylethyl)-2 H-tetrazol-5-yl]biphenyl-4-carbaldehyde (0.5102 g, 1.67 mmol), as an oil.

Proceeding as in Example 5 but replacing 1-(1,1-dimethylethyl)-5-(2 -methoxyphenyl)-1H-tetrazole with 5-(2-methoxyphenyl)-1-(1-methyl-1-phenylethyl)-2H-tetrazole gave 2'-[2-(1-methyl-1-phenylethyl)-2H-tetrazol-5-yl]biphenyl-4-carbaldehyde as an oil.

Proceeding as in Example 5 but replacing 1-(1,1-dimethylethyl)-5-(2-methoxyphenyl)-2H-tetrazole with 5-(2-methoxyphenyl)-1-triphenylmethyl-1H-tetrazole gave 2'-[2-(triphenylmethyl)-2H-tetrazol-5-yl]biphenyl-4-carbaldehyde as an oil.

EXAMPLE 6

2'-[2-(1-Methyl-1-phenylethyl)-2H-tetrazol-5-yl] biphenyl-4-carbaldehyde

The following is the preparation of a protected 2'-(2H-tetrazol-5-yl)-biphenyl-4-carbaldehyde in which the protective group is 1-methyl-1-phenylethyl.

A solution of 1-bromo-4-dimethoxymethylbenzene (2.24 g, 9.7 mmol), prepared as in Example 2, in 20 mL of dry diethyl ether was cooled to between −60° and −65° C. under nitrogen and n-butyllithium (6.3 mL, 1.6M in hexane, 10.0 mmol) was added over 5 minutes. The reaction mixture was held at −40° C. to −35° C. for 30 minutes and then 5-(2-methoxyphenyl)-1-(1-methyl-1-phenylethyl)-1 H-tetrazole (2.4 g, 8.01 mmol), prepared as in Example 3, in 5.0 mL of diethyl ether was added. The mixture was allowed to warm to room temperature and then stirred for 2 hours. The reaction was quenched with saturated ammonium chloride and extracted with ethyl acetate and concentrated. Purification by column chromatography on silica gel (elution: 10% ethyl acetate in hexane) gave 4-dimethoxymethyl-2'-[2-(1-methyl-1-phenylethyl)-2H-tetrazol-5-yl]biphenyl as an oil.

A solution of 4-dimethoxymethyl-2'-[2-(1-methyl-1-phenylethyl)-2H-tetrazol-5-yl]biphenyl (2.9 g, 7.0 mmol) and 15 mL of 4M hydrochloric acid in 50 mL of methanol was stirred at room temperature for 18 hours. The mixture was diluted with 200 mL of diethyl acetate and poured into 300 mL of water. The ethyl acetate layer was washed 3 times with water, dried over magnesium sulfate and concentrated giving a white, waxy solid (2.51 g). A portion of the solid (1.53 g) was crystallized from diethyl ether and isolated. Drying gave 2'-[2-(1-methyl-1-phenylethyl)biphenyl-2H-tetrazolebiphenyl-4-carbaldehyde (1.2 g, 3.2 mmol), m.p. 98.5°–97° C.

EXAMPLE 7

1-Butylindole-3-carboxylic Acid

A suspension of sodium hydride (34.1 g, 1.42 mol) in 300 mL of DMF was stirred in an ice/methanol bath and a solution of 3-indolecarboxylic acid (55.0 g, 0,374 mol) in 250 mL DMF was added dropwise over 45 minutes. The mixture was stirred for 30 minutes and then 100 mL of additional DMF was added. The mixture was cooled to 0° C. and 1-iodobutane (8.79 g, 40.8 mL, 0.359 mol) was added. The mixture was stirred for approximately 12 hours. The mixture was then poured in 2.0 L of ice water, acidified with 1N hydrochloric acid, extracted 3 times with ethyl acetate, washed twice with water and then dried over magnesium sulfate. The mixture was concentrated and the residue mixed with diethylether. Filtration gave 1-butylindole-3-carboxylic acid (62.74 g, 0.309 mol) as a white powder.

EXAMPLE 8

1-Butyl-2-{2'-[2-(triphenylmethyl)-2H-tetrazol-5-yl] biphenyl-4-ylmethyl}-1 H-indole-3-carboxylic Acid Step (a)

A solution of 1-butyl-3-indolecarboxylic acid (217 g, 1.56 mol), prepared as in Example 7, in 8 L of THF was cooled under nitrogen to −60° C. n-Butyllithium (1.6N in hexane, 1.3 L, 2.1 mol) was added at a rate such that the reaction temperature remained below −20° C. and then the mixture was allowed to warm to −8° C. The mixture cooled again to −60° C. and 2'-[2-(triphenylmethyl)-biphenyl-2 H-tetrazolebiphenyl-4-carbaldehyde (292 g, 0.956 mol), prepared as in Example 5 or 6, in 1.5 L of THF was added. The mixture was allowed to warm to −30° C. and stirred for 1 hour. The mixture was diluted with 8 L of water and then extracted with ethyl acetate (1×3 L). The aqueous layer was extracted with ethyl acetate (1×4 L) and the combined organic layers were washed with 4 L of water containing 1 L of sodium chloride solution. The organic layer was then washed with 3 L of water containing 50 mL of concentrated hydrochloric acid. The organic layer was washed again with saturated sodium chloride solution and concentrated by evaporation under vacuum. The residue was combined with 3 L of hexanes and the mixture was cooled to 0° C. and stirred for 3 hours giving a precipitate. The precipitate was isolated by filtration and washed with hexane (3×500 mL). Drying at 40° C. with a nitrogen bleed gave gave 1-butyl-2-{2 '-[2-(triphenylmethyl)-2H-tetrazol-5-yl]biphenyl-4-yl-(hydroxy)methyl}-1H-indole-3-carboxylic acid (395.2 g, 0.56 mol).

Step (b)

A mixture of 1-butyl-2-{2'-[2-(triphenylmethyl)-2H-tetrazol-5-yl]-biphenyl-4 -yl(hydroxy)methyl}-1H-indole-3-carboxylic acid (2.5 g, 3.52 mmol) and 10% palladium on carbon (1.2 g) in 20 mL of acetic acid and 80 mL of THF under a hydrogen atmosphere (200 psi) at 48° C. for approximately 48 hours. The mixture was then cooled, filtered and diluted with 500 mL of water. The mixture was extracted with 100 mL of ethyl acetate and the ethyl acetate layer was washed three times with water. The ethyl acetate layer was concentrated to give 1-butyl-2-[2'-(2H-tetrazol-5-yl)biphenyl-4-ylmethyl]-1H-indole-3-carboxylic acid (1.2 g, 2.66 mmol).

EXAMPLE 9

1-Butyl-2-[2'-(2H-tetrazol-5-yl)biphenyl-4 -ylmethyl]-1H-indole-3-carboxylic Acid A mixture of 1-butyl-2-{2'-[2-(1-methyl-1-phenyl)-2H-tetrazol-5-yl] -biphenyl-4-ylmethyl}-1H-indole-3-carboxylic acid (8.0 g, 0.0141 mol), pentaerythritol tetrakis(2-mercaptoacetate) (4.84 mL, 0.0155 mol) and boron trifluoride etherate (6.92 mL, 0.056 mol) in 120 mL of acetonitrile was stirred at room temperature for 1.5 hours. The reaction mixture was partitioned between 180 mL of 1M sodium hydroxide and 40 mL of ethyl acetate. The sodium hydroxide layer was stirred and 3M hydrochloric acid was added giving a crystalline product. The product was isolated by filtration and the filter cake was washed 3 times with 30 mL each of methanol. Drying gave 1-butyl-2-[2'-(2H-tetrazol-5 -yl)biphenyl-4-ylmethyl]-1H-indole-3-carboxylic acid (5.9 g, 0.0131 mol), m.p. 228°–230° C. dec.

We claim:

1. A process for the preparation of 1-butyl-2-[2'-(2H-tetrazol-5-yl)-biphenyl-4-ylmethyl] -1H-indole-3-carboxylic acid which process comprises:
(A) (i) treating 1-butyl-1H-indole-3-carboxylic acid with an organometallic base to give 2-metalated 1-butyl-1H-indole-3-carboxylic acid,
   (ii) optionally treating the 2-metalated 1-butyl-1H-indole-3-carboxylic acid with a metal halide to give 2-transmetalated 1-butyl-1H-indole-3-carboxylic acid and
   (iii) reacting the 2-metalated or 2-transmetalated 1-butyl-1H-indole-3-carboxylic acid with protected 2'-(2H-tetrazol-5-yl)biphenyl-4-carbaldehyde to give protected 1-butyl-2-[2'-(2H-tetrazol-5-yl)biphenyl-4-yl(hydroxy)methyl]-1 H-indole-3-carboxylic acid;
(B) dehydroxylating to give protected 1-butyl-2-[2'-(2H-tetrazol-5-yl)-biphenyl-4 -ylmethyl]-1H-indole-3-carboxylic acid and
(C) deprotecting.

2. The process of claim 1 which comprises:
(A) (i) treating 1-butyl-1H-indole-3-carboxylic acid with n-butyllithium to give 2-lithiated 1-butyl-1H-indole-3-carboxylic acid and
   (ii) reacting the 2-lithiated 1-butyl-1H-indole-3-carboxylic acid with protected 2'-[2-(1-methyl-1-phenylethyl)-2H-tetrazol-5-yl]biphenyl-4-carbaldehyde to give 1-butyl-2-{2'-[2-(1-methyl-1-phenylethyl)-2H-tetrazol-5 -yl]biphenyl-4-yl(hydroxy)methyl}-1H-indole-3-carboxylic acid;
(B) dehydroxylating to give 1-butyl-2-{2'-[2-(1-methyl-1-phenylethyl)-2H-tetrazol-5 -yl]biphenyl-4-ylmethyl}-1H-indole-3-carboxylic acid and
(C) deprotecting.

3. The process of claim 2 in which deprotecting comprises reacting the protected 1-butyl-2-[2'-(2H-tetrazol-5-yl)biphenyl-4-ylmethyl]-1H-indole-3-carboxylic acid with a Lewis acid in the presence of a thiol.

4. The process of claim 3 in which the Lewis acid is boron trifluoride etherate, tin(IV)chloride, titanium(IV)chloride, titanium(III)chloride, zinc chloride or selenium(IV)chloride and the thiol is methyl thioglycolate, pentaerythritol tetrakis(2-mercaptoacetate), $(C_{1-4})$alkanethiol, arylthiol, 2-mercaptoacetic acid or $(C_{1-4})$alkyl 2-mercaptoacetate.

5. The process of claim 4 in which the Lewis acid is boron trifluoride etherate and the thiol is methyl thiogylcolate or pentaerythritol tetrakis(2-mercaptoacetate).

6. A process for the preparation of protected 2'-(2H-tetrazol-5-yl)-biphenyl-4-carbaldehyde, which process comprises:
(i) treating a compound of Formula I:

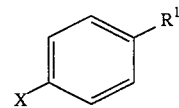

in which X is halo and $R^1$ is 1-isopropyl-2-methylpropyliminomethyl or dimethoxymethyl with an organometallic base to give a corresponding para-metalated intermediate,
(ii) optionally treating the para-metalated intermediate with a metal halide to give a para-transmetalated compound of Formula I;
(iii) reacting the para-metalated or para-transmetalated intermediate with a compound of Formula II:

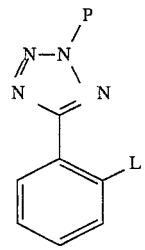

in which L is a leaving group and P is a protective group, and acidifying.

7. The process of claim 6 which comprises:
(i) treating (4-bromobenzylidene)(1-isopropyl-2-methylpropyl)amine with n-butyllithium to give para-lithiated (benzylidene)(1-isopropyl-2-methylpropyl)amine and
(ii) reacting the para-lithiated (benzylidene)(1-isopropyl-2-methylpropyl)amine with 5-(2-methoxyphenyl)-2-(1-methyl-1-phenylethyl)-2H-tetrazole and acidifying.

8. A process for the preparation of 1-butyl-2-[2'-(2 H-tetrazol-5-yl)biphenyl-4-ylmethyl]-1H-indole-3-carboxylic acid which process comprises:
(A) (i) treating a compound of Formula I:

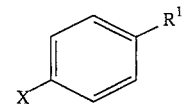

in which X is halo and $R^1$ is 1-isopropyl-2-methylpropyliminomethyl or dimethoxymethyl with an organometallic base to give a corresponding para-metalated intermediate,
(ii) optionally treating the para-metalated intermediate with a metal halide to give a para-transmetalated intermediate;
(iii) reacting the para-metalated or para-transmetalated intermediate with a compound of Formula II:

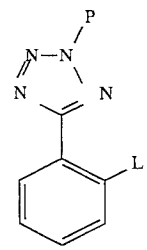

in which L is a leaving group and P is a protective group, and acidifying to give protected 2'-(2H-tetrazol-5-yl)biphenyl-4-carbaldehyde;
(B) reacting the protected 2'-(2H-tetrazol-5-yl)biphenyl-4-carbaldehyde with 2-metalated or 2-transmetalated 1-butyl-1H-indole-3-carboxylic acid to give protected 1-butyl-2-[2'-(2H-tetrazol-5-yl)biphenyl-4-yl(hydroxy)methyl]-1H-indole-3 -carboxylic acid;
(C) dehydroxylating to give protected 1-butyl-2-[2'-(2H-tetrazol-5-yl)biphenyl-4-ylmethyl] -1H-indole-3-carboxylic acid and
(D) deprotecting.

9. The process of claim 8 which comprises:
(A) (i) treating (4-bromobenzylidene)(1-isopropyl-2-methylpropyl)amine with n-butyllithium to give para-lithiated (4-bromobenzylidene)(1-isopropyl-2-methylpropyl)amine and
(ii) reacting the para-lithiated (4-bromobenzylidene)(1-isopropyl-2-methylpropyl)amine with 5-(2-methoxyphenyl)-2-(1-methyl-1-phenylethyl)-2H-tetrazole and acidifying to give 2'-[2-(1-methyl-1-phenylethyl)-2H-tetrazol-5-yl]biphenyl-4 -carbaldehyde;
(B) reacting the 2'-[2-(1-methyl-1-phenylethyl)-2H-tetrazol-5-yl]biphenyl-4 -carbaldehyde with 2-lithiated 1-butyl-1H-indole-3-carboxylic acid to give 1-butyl-2-{2'-[2-(1-methyl-1-phenylethyl)-2H-tetrazol-5-yl]methyl] }1H-indole-3-carboxylic acid;
(C) dehydroxylating to give 1-butyl-2-{2'-[2-(1-methyl-1-phenylethyl)-2H-tetrazol-5 -yl]biphenyl-4-yl-(hydroxy)methyl]}1H-indole-3-carboxylic acid and
(D) deprotecting.

10. The process of claim 9 in which deprotecting comprises reacting the 1-butyl-2-{2'-[2-(1-methyl-1-phenylethyl)-2H-tetrazol-5-yl]biphenyl-4 -ylmethyl}-1H-indole-3-carboxylic acid with a Lewis acid in the presence of a thiol.

11. The process of claim 10 in which the Lewis acid is boron trifluoride etherate, tin(IV)chloride, titanium(IV)chloride, titanium(III)chloride, zinc chloride or selenium(IV)chloride and the thiol is methyl thioglycolate, pentaerythritol tetrakis(2-mercaptoacetate), $(C_{1-4})$alkanethiol, arylthiol, 2-mercaptoacetic acid or $(C_{1-4})$alkyl 2-mercaptoacetate.

12. The process of claim 11 in which the Lewis acid is boron trifluoride etherate and the thiol is methyl thioglycolate or pentaerythritol tetrakis(2-mercaptoacetate).

13. A compound which is protected 2'-(2H-tetrazol-5-yl)biphenyl-4-carbaldehyde.

14. The compound of claim 13 in which the protective group is 1-methyl-1-phenylethyl, namely 2'-[2-(1-methyl-1-phenylethyl)biphenyl-2H-tetrazole-biphenyl-4-carbaldehyde.

15. A compound of Formula II:

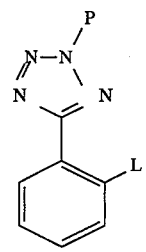

in which L is a leaving group and P is a protective group.

16. The compound of claim 15 in which L is methoxy.

17. The compound of claim 16 in which P is 1-methyl-1-phenylethyl.

* * * * *

UNITED STATES PATENT AND TRADEMARK OFFICE
CERTIFICATE OF CORRECTION

PATENT NO. : 5,468,867

DATED : November 21, 1995

INVENTOR(S) : Fisher, et al.

It is certified that error appears in the above-identified patent and that said Letters Patent is hereby corrected as shown below:

Claim 9, at column 15, line 25 "tetrazol-5-yl]methyl]" should read --tetrazol-5-yl]biphenyl-4-yl-(hydroxy)methyl]--.

Signed and Sealed this

Nineteenth Day of March, 1996

*Attest:*

BRUCE LEHMAN

*Attesting Officer     Commissioner of Patents and Trademarks*